United States Patent [19]

Hedgecock et al.

[11] Patent Number: 5,247,079
[45] Date of Patent: Sep. 21, 1993

[54] 7-CYCLOPROPYL-IMIDAZODIAZEPINES

[75] Inventors: Charles J. R. Hedgecock; Stuart D. Jones, both of Swindon, Great Britain

[73] Assignee: Roussel Uclaf, France

[21] Appl. No.: 781,755

[22] Filed: Oct. 23, 1991

[30] Foreign Application Priority Data

Oct. 24, 1990 [GB] United Kingdom ............... 9023155

[51] Int. Cl.⁵ .................. C07D 487/04; A61K 31/55
[52] U.S. Cl. .................................................. 540/498
[58] Field of Search ....................................... 540/498

[56] References Cited

U.S. PATENT DOCUMENTS 4,868,176 9/1989 Gardner et al. ................ 540/498

Primary Examiner—Robert T. Bond
Attorney, Agent, or Firm—Bierman and Muserlian

[57] ABSTRACT

A compound selected from the group consisting of a compound of the formula

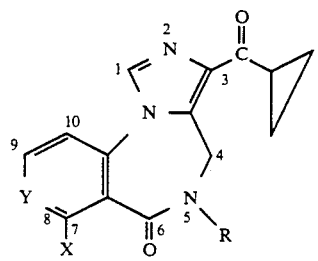

wherein Y is a nitrogen atom or carbon atom bearing Z, Z is selected from the group consisting of hydrogen, halogen, $-C\equiv N$, $-N_3$ and $-C(Hal)_3$, Hal is a halogen, X is cycloalkyl of 3 to 6 carbon atoms or hydrogen with the proviso that when X is hydrogen, Y must be nitrogen. R is selected from the group consisting of hydrogen, alkyl of 1 to 5 carbon atoms, phenyl and substituted phenyl and their non-toxic, pharmaceutically acceptable acid addition salts, a process and intermediate for preparing them, having tranquillizing properties.

6 Claims, No Drawings

7-CYCLOPROPYL-IMIDAZODIAZEPINES

OBJECTS OF THE INVENTION

It is an object of the invention to provide the novel compounds of formula I and their non-toxic, pharmaceutically acceptable acid addition salts and novel processes and intermediates for their preparation.

It is another object of the invention to provide novel transquillizing compositions and a novel method of inducing tranquillity in warm-blooded animals.

These and other objects and advantages of the invention will become obvious from the following detailed description.

THE INVENTION

The novel compounds of the invention are a compound selected from the group consisting of a compound of the formula

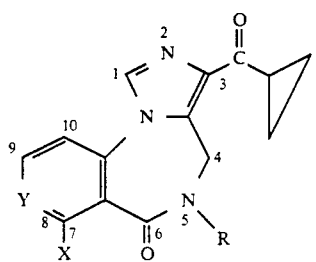

I wherein Y is a nitrogen atom or carbon atoms bearing Z, Z is selected from the group consisting of hydrogen, halogen, —C≡N, —N₃ and —C(Hal)₃, Hal is a halogen, X is cycloalkyl of 3 to 6 carbon atoms or hydrogen, with the proviso that when X is hydrogen, Y must be nitrogen, R is selected from the group consisting of hydrogen, alkyl of 1 to 5 carbon atoms, phenyl and substituted phenyl and their non-toxic-pharmaceuticlly acceptable acid addition salts.

Examples of halogen are fluorine, chlorine and bromine and examples of cycloalkyl include cyclopropyl, cyclobutyl, cyclopentyl and cyclohexyl. Examples of alkyl of 1 to 5 carbon atoms are methyl, ethyl, n-propyl, isopropyl, butyl, iso-butyl, tert-butyl and linear and branched pentyl. The phenyl substituents include halogen, alkyl and alkoxy of 1 to 3 carbon atoms and —CF₃. Examples of alkyl and alkoxy of 1 to 3 carbon atoms are methyl, ethyl, n-propyl, isopropyl, methoxy, ethoxy, propoxy and isopropoxy.

Examples of the acids for the formation of the non-toxic, pharmaceutically acceptable acid addition salts are inorganic acids such as hydrochloric acid, hydrobromic acid, hydroiodic acid, nitric acid, sulfuric acid and phosphoric acid and organic acids such as formic acid, acetic acid, propionic acid, benzoic acid, maleic acid, fumaric acid, succinic acid, tartaric acid, citric acid, oxalic acid, glyoxylic acid, aspartic acid, alkane sulfonic acids such as methane sulfonic acid and aryl sulfonic acids such as benzene sulfonic acid.

Among the preferred compounds of formula I are those wherein Y is a nitrogen or carbon atom bearing Z and Z is hydrogen and those wherein X is cyclopropyl and their acid addition salts. Specific preferred compounds of formula I are 7-cyclopropyl-5,6-dihydro-5-methyl-6-oxo-4H-imidazo-[1,5-a][1,4]-benzodiazepin-3-yl cyclopropyl methanone; and 7-cyclopropyl-5,6-dihydro-5-methyl-6-oxo-4H-imidazo-[1,5-a]-pyrido[3,4-f]diazepin-3-yl cyclopropyl methanone and the acid addition salts thereof.

The novel process of the invention for the preparation of compounds of the formula

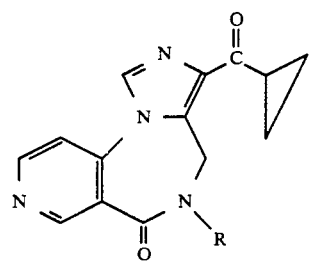

I$_A$ wherein R is as defined above comprises oxidizing a compound of the formula

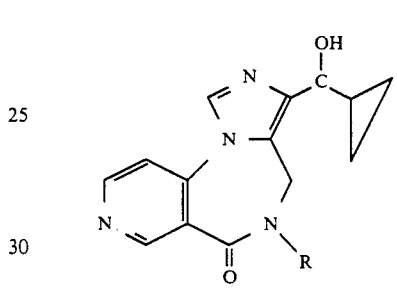

II wherein R is as defined above. The oxidation of the compound of formula II may be conveniently effected with manganese dioxide.

The compound of formula II may be prepared by reacting a compound of the formula

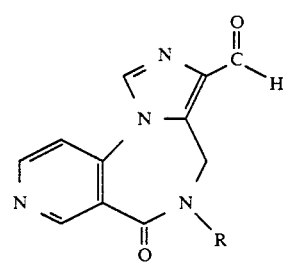

III wherein R is as defined above with the magnesium derivative of a compound of the formula

IV wherein Hal is halogen. The reaction between the compound of formula III and the magnesium derivative of the compound of formula IV may be effected in the presence of an anhydrous organic solvent such as tetrahydrofuran.

The compounds of formula I$_A$ may also be prepared by reacting a compound of the formula

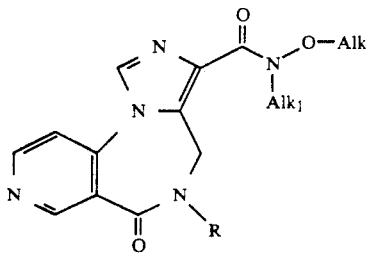

V wherein Alk and Alk₁ are individually alkyl of 1 to 3 carbon atoms and R is as defined above with the magnesium derivative of a compound of formula IV as defined above. The reaction between the compound of formula V and the magnesium derivative of the compound of formula IV may be effected as indicated above for the reaction with the compound of formula III.

The process for the preparation of a compound of the formula

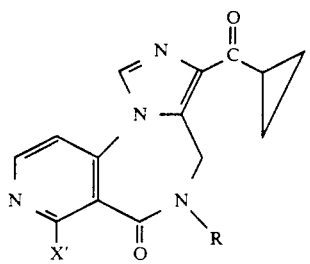

$I_B$ wherein X' is cycloalkyl of 3 to 6 carbon atoms and R is as defined above comprises oxidizing a compound of the formula

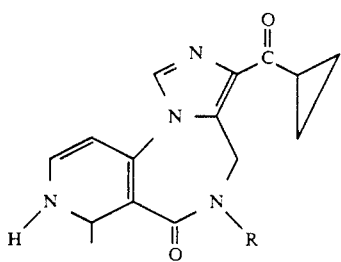

VI wherein X' and R are as defined above. Oxidation of the compound of formula VI may be effected with a mild oxidizing reagent such as manganese dioxide The oxidation may be effected in the presence of an anhydrous organic solvent such as dichloromethane.

The compound of formula VI may be prepared by reacting a compound of formula $I_A$ as defined above with the magnesium derivative of a compound of the formula Hal-X'  VII wherein Hal and X' are as defined above. The reaction between the compound of formula $I_A$ and the compound of formula VII may be effected in the presence of an anhydrous organic solvent such as tetrahydrofuran.

The compounds of formula $I_A$ may be prepared, for example, by the processes above. A compound of formula $I_B$ in which X' is cyclopropyl is preferably prepared in a single step by reacting a compound of formula V as defined above with an excess of the magnesium derivative of a compound of formula IV. The reaction between the compound of formula V and the magnesium derivative of the compound of formula IV may be effected in the presence of an anhydrous organic solvent such as tetrahydrofuran.

The process for the preparation of a compound of the formula

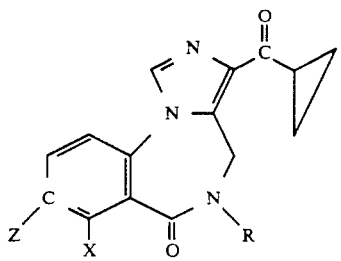

$I_C$ wherein Z, X and R are as defined above comprises reacting a compound of the formula

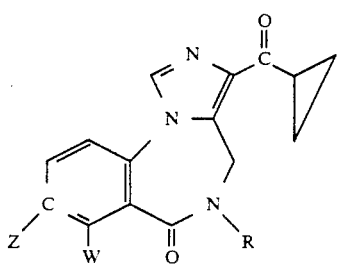

VIII wherein W is fluorine or chlorine and Z and R are as defined above with the magnesium derivative of a compound of formula VII. In the compound of formula VIII, W preferably is fluorine. The reaction between the compound of formula VIII and the compound of formula VII may be effected in the presence of an anhydrous organic solvent such as tetrahydrofuran.

The compounds of formula VIII may be prepared by reacting a compound of the formula

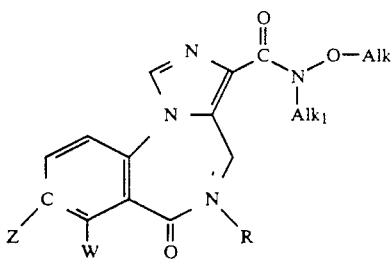

IX wherein Z, W, R, Alk and Alk₁ are as defined above with the magnesium derivative of a compound of formula IV.

The compounds of formula $I_C$ in which X is cyclopropyl are preferably prepared in a single step by reacting a compound of formula IX as defined above with an excess of the magnesium derivative of the compound of formula IV. The reaction between the compound of formula IX and the compound of formula IV may be effected in the presence of an anhydrous organic solvent such as tetrahydrofuran.

The compounds of formula VIII may alternatively be prepared by oxidizing a compound of the formula

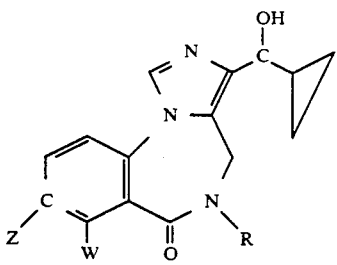

(X)

wherein Z, W and R are as defined above. Oxidation of the compound of formula X may be effected with manganese dioxide as indicated for oxidation of the compound of formula VI.

The compounds of formula X may be prepared by reacting a compound of the formula

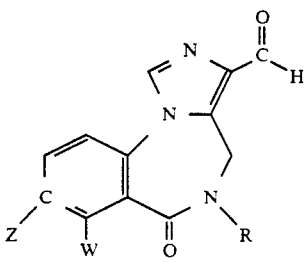

(XI)

wherein Z, W and R are as defined above with the magnesium derivative of the compound of formula IV. The reaction between the compound of formula XI and the magnesium derivative of formula IV may be effected in the presence of an anhydrous organic solvent such as tetrahydrofuran.

The compounds of formula V and IX may be prepared for example, by a process analogous to that described in European Patent Application No. 90403526.8 according to the folllowing reaction scheme:

pean Patent No. 27214 or by processes analogous to these.

The compounds of formula I may, if desired, be converted into their acid addition salts by reacting the compounds of formula I with an inorganic or organic acid, for example, in approximately stoichiometric proportions. The salts may be prepared without intermediate isolation of the corresponding base.

The tranquillizing compositions of the invention are comprised of a tranquillizingly effective amount of at least one compound of formula I and its non-toxic pharmaceutically acceptable addition salts and an inert pharmaceutical carrier. The compositions may be in the form of tablets, dragees, capsules, granules, suppositories and injectable solutions or suspensions.

Examples of suitable excipients are talc, gum arabic, lactose, starch, magnesium stearate, cocoa butter, aqueous or non-aqueous vehicles, animal or vegetable fats, paraffin derivatives, glycols, various wetting, dispersing or emulsifying agents and/or preservatives.

The compositions also possess benzodiazepine inverse antagonistic properties. The compositions are useful in the treatment of memory disorders, particularly in the treatment of geriatrics, and in the treatment of cerebral senescence. Some of the compounds can also be used in the treatment of obesity and also as mild tranquillizers in the treatment of irritability and certain agitated conditions and certain forms of epilepsy.

The novel method of inducing tranquillization in warm-blooded animals comprises administering to warm-blooded animals a tranquillizingly effective amount of at least one compound of formula I and its non-toxic pharmaceutically acceptable acid addition salts. The compounds may be administered orally, rectally or parenterally. The usual daily dose is 0.0013 to 2.66 mg/kg depending upon the condition treated, the specific compound and the method of administration.

Another method of the invention for the treatment of a patient suffering from, or susceptible to memory disorders, cerebral senescence problems, obesity, agitated

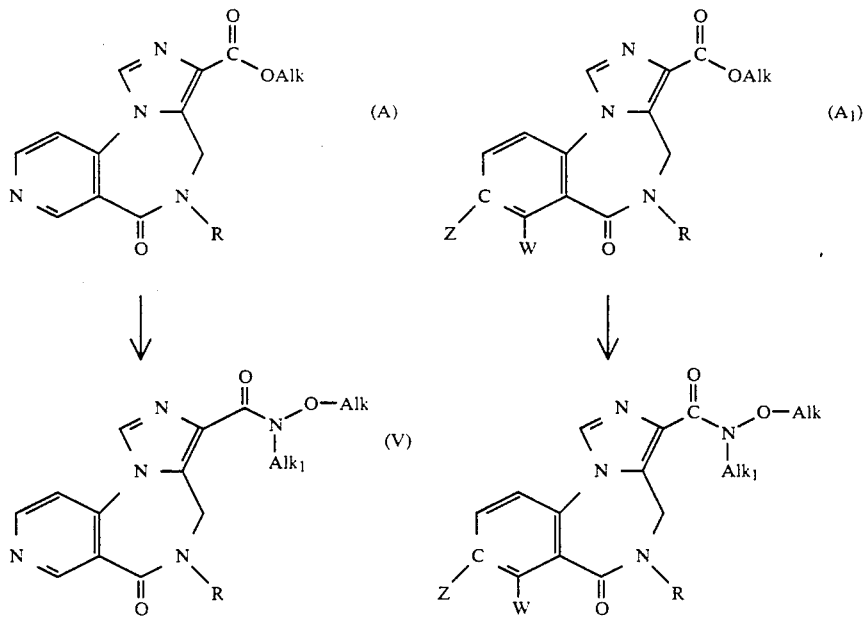

wherein R, Alk, Alk$_1$, W and Z are as defined above. The compounds of formulae III and XI may be prepared, for example, by the processes described in Euroconditions, irritability or epilepsy comprises administering to the patient an effective amount of a compound of formula I as defined above or a pharmacologically acceptable acid addition salt thereof.

The novel intermediates of the invention are compounds of the formula

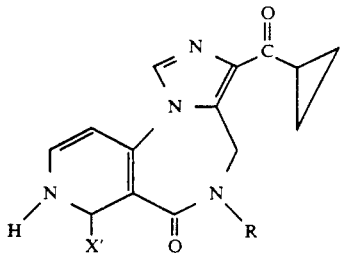

wherein X' and R are as defined above; compounds of the formula

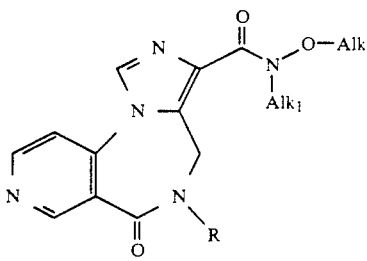

wherein R, Alk and Alk₁ are as defined above; and compounds of the formula

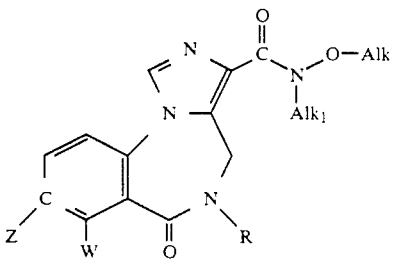

In the following examples there are described several preferred embodiments to illustrate the invention. However, it should be understood that the invention is not intended to be limited to the specific embodiments.

EXAMPLE 1

7-cyclopropyl-5,6-dihydro-5-methyl-6-oxo-4H-imidazo benzodiazeoin-3-yl cyclopropyl methanone To a solution of cyclopropyl magnesium bromide (prepared from 905 mg of magnesium and 1.63 g of cyclopropyl bromide in 25 ml of dry THF at 0° C. was added 3.4 g of methyl 7-fluoro-5,6-dihydro-5-methyl-6-oxo-4H-imidazo[1,5-a][1,4]benzodiazepin-3-yl N-methylcarbohydroxamate and the mixture was stirred for 30 minutes before quenching with ammonium chloride solution and extracting with ethyl acetate. The organic solution was dried with magnesium sulfate and evaporated to an oil which on chromatography (SiO₂-dichloromethane: ethyl acetate 1:1) gave 680 mg (20% yielded) of the desired compound melting at 204° C. to 205° C.

IR KBr disc) 3095, 1634, 1562, 1490, 1360, 1253, 974, 935 cm⁻¹ ¹Hnmr. (CDCl₃) 7.89 (1H,s); 7.46 (1H,t); 7.17 (1H,d); 7.06 (1H,d); 5.25 (1H,d); 4.32 (1H,d); 3.18 (4H,s+m); 2.39 (1H,m); 0.95-1.3 (6H,m); 0.84 (1H,m); 0.67 (1H,m).

| Analysis: $C_{19}H_{19}N_3O_2$ | | | |
|---|---|---|---|
| Calculated: | % C 71.01 | % H 5.96 | % N 13.08 |
| Found: | 70.76 | 6.05 | 12.9 |

EXAMPLE 2

7-cyclopropyl-5,6-dihydro-5-methyl-6-oxo-4H-imidazo-[1,5-a]pyrido 3,4-f] diazepin-3-yl cyclopropyl methanone STEP A:
7-cyclopropyl-5,6,7,8-tetrahydro-5-methyl-6-oxo-4H-imidazo [1,5-a] pyrido [3,4-f] diazeoin-3-yl-cyclopropyl methanone To a solution of 305 mg of methyl (5,6-dihydro-5-methyl-6-oxo-4H-imidazo-[1,5-a]-pyrido-[3,4-f]-diazepin-3-yl) N-methyl-carbohydroxamate in 10 ml of dry tetrahydrofuran at room temperature was added a solution of cyclopropyl magnesium bromide prepared from 72 mg of Mg and 450 mg of cyclopropyl bromide in 10 ml of dry tetrahydrofuran and the mixture was stirred for 1 hour at room temperature. 10 ml of saturated ammonium chloride were added and the mixture was partitioned between water and dichloromethane. The organic solution was dried over magnesium sulfate and evaporated to an oil. Flash chromatography (SiO₂-ethyl acetate/dichloromethane 1:1) yielded 104 mg of 7-cyclopropyl-5,6,7,8-tetrahydro-5-methyl -6-oxo-4H-imidazo-1,5-a]-pyrido-[3,4-f]-diapzepin-3-yl cyclopropyl methanone (34% yield).

STEP B:
7-cyclopropyl-5,6-dihydro-5-methyl-6-oxo-4H-imidazo-[[1,5-a] -pyrido-[3,4-f]-diazepin-3-yl cyclopropyl methanone To a solution of 78 mg of the above intermediate in 6 ml of dichloromethane was added 400 mg of manganese dioxide and the mixture was stirred at room temperature for 1.5 hours. The solution was filtered and evaporated to dryness. Flash chromatography (SiO₂-dichloromethane/diethyl ether/methanol 50/50/1) yielded 61 mg of the desired compound (78% yield) melting at 235° C. to 237° C.

IR Spectrum (KBr disc)

1643, 1566, 1550, 1490, 1420, 1386, 1203, 1042, 967 cm⁻¹. ¹Hnmr (CDCl₃) 8.57 (1H,d); 7.93 (1H,s); 7.04 (1H,d); 5.32 (1H,d); 4.38 (1H,d); 3.17 (4H,s+m); 2.51 (1H,m); 1.7 (8H,m).

| Analysis: $C_{18}H_{18}N_4O_2$ | | | |
|---|---|---|---|
| Calculated: | % C 67.07 | % H 5.63 | % N 17.38 |
| Found: | 66.6 | 5.65 | 17.21 |

EXAMPLE 3

5,6-dihydro-5-methyl-6-oxo-4H-imidazo-[1,5-a]-pyrido-3,4-f1-diazepin-3-yl-cyclopropyl-methanone

STEP A:

5,6-dihydro-5-methyl-6-oxo-4H-imidazo-1,5-a1-pyrido-[3,4-f]-diazepin-3-yl cyclopropyl carbinol To a solution of cyclopropyl magnesium bromide in dry tetrahydrofuran (prepared from 72 mg (3 mmole)) of magnesium and 362 mg (3 mmole) of cyclopropyl bromide in 4 ml of tetrahydrofuran was added at room temperature in one portion a suspension of 240 mg (1 mmole) of 5,6-dihydro-5-methyl-6-oxo-4H-imidazo [1,5-a]-pyrido [3,4-f][1,4]-diazepine-3-carboxaldehyde suspended in a mixture of 1 ml of tetrahydrofuran and 1 ml of hexamethyl-phosphoramide. After 1 hour, the reaction was quenched with aqueous ammonium chloride and extracted with dichloromethane. Column chromatography (SiO$_2$-5% methanol in dichloromethane) yielded 120 mg of 5,6-dihydro-5-methyl-6-oxo-4H-imidazo-1,5-a]-pyrido-[3,4-f][1,4]-diazepin-3-yl cyclopropyl carbinol as an oil, (43%).

STEP B: 5,6-dihydro-5-methyl-6-oxo-4H-imidazo [1,5-a1-pyrido [3,4-f]-diazepin-3-yl cyclopropylmethanone.

To a solution of 100 mg (0.35 mmole) 5,6-dihydro-5-methyl-6-oxo-4H-imidazo-[1,5-a]-pyrido[3,4-f]-diazepine-3-yl cyclopropyl carbinol in 15 ml of dichloromethane was added 600 mg of mangnese dioxide and the mixture was refluxed for 40 minutes before cooling and filtering. Evaporation of solvent and crystallization by addition of ether gave 84 mg of 5,6-dihydro-5-methyl-6-oxo-4H-imidazo [1,5-a]-pyrido-[3,4-f][1,4]-diazepin-3-yl cyclopropylmethanone (85%) melting at 237° C. to 238° C.

IR (KBR DISC): 1645, 1564, 1489, 1383, 1170, 1010, 964 cm$^{-1}$ $^1$Hnmr (CDCl$_3$) 9.28 (1H,s); 8.85 (1H,d); 7.97 (1H,s); 7.36 (1H,d); 4.88 (2H,bs); 3.26 (3H,s); 3.18 (1H,m); 1.25 (2H,m); 1.12 (2H,m).

| Analysis: C$_{15}$H$_{14}$N$_4$O$_2$.¼H$_2$O | | | |
|---|---|---|---|
| Calculated: | % C 62.82 | % H 5.10 | % N 19.53 |
| Found: | 62.97 | 5.12 | 19.43 |

EXAMPLE 4

Tablets were prepared containing 20 mg of the compound of Example 1 or 2 and sufficient excipient of lactose, starch, talc and magnesium stearate for one tablet weighing 150 mg.

Biochemical Activity

Test 1

The affinity of the active ingredients for the benzodiazepine receptors was measured using a radioactively labelled ($^3$H) compound flunitrazepam, and a modified version of the method of Squires and Braestrup (*Nature*, 1977, Vol. 266, p. 732). The values given in Table 2 below are the concentration (mol × 10$^{-9}$) of the compound under test which inhibited 50% of the specific binding of 0.6 × 10$^{-9}$ mol of $^3$H-labelled flunitrazepam in preparations of membranes from the rear portion of the brain in rats (IC$_{50}$ values).

Test 2

Measuring of in vivo binding to benzodiazepine receptors was carried out according to the method described by Goeders et al, Life Sciences (1985), Vol. 37, p. 345.

TABLE 2

| Example | Test 1 | Test 2 ED$_{50}$ mg/kg IP |
|---|---|---|
| 1 | 36 | 0.15 |
| 2 | 26 | 0.08 |
| 3 | 105 | 0.13 |

Various modifications of the products and method of the invention may be made without departing from the spirit or scope thereof and it is to be understood that the invention is intended to be limited only as defined in the appended claims.

What is claimed is:

1. A compound selected from the group consisting of a compound of the formula

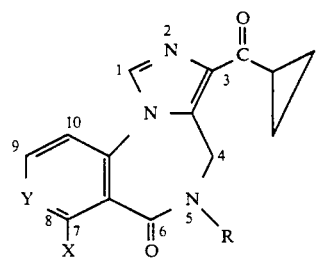

wherein Y is a nitrogen atom or carbon atom bearing Z, Z is selected from the group consisting of hydrogen, halogen, —C≡N, —N$_3$ and —C(Hal)$_3$, Hal is a halogen, X is cyclopropyl R is selected from the group consisting of hydrogen, alkyl of 1 to 5 carbon atoms, phenyl and phenyl substituted with at least one member of the group consisting of halogen, alkyl and alkoxy of 1 to 3 carbon atoms and —CF$_3$ and their non-toxic, pharmaceutically acceptable acid addition salts.

2. A compound of claim 1 wherein Z is hydrogen.

3. A compound of claim 1 wherein X is cyclopropyl.

4. A compound of claim 1 selected from the group consisting of 7-cyclopropyl-5,6-dihydro-5-methyl-6-oxo-4H-imidazo-[1,5a][1,4]-benzodiazepin-3-yl cyclopropyl methanone; and ·7-cyclopropyl-5,6-dihydro-5-methyl-6-oxo-4H-imidazo-[1,5-a]-pyrido-[3,4-f]-diazepin-3-yl cyclopropyl metanone; and their non-toxic, pharmaceuticaly acceptable acid addition salts.

5. A compound having a formula selected from the group consisting of

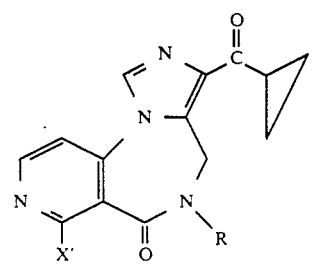

VI

-continued
V
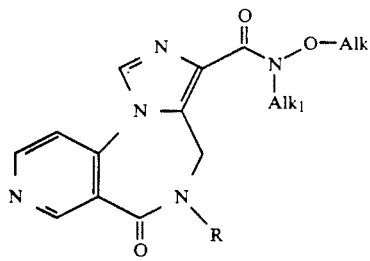
and
-continued
IX
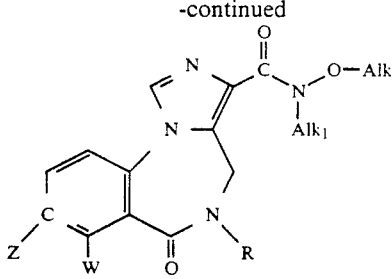
wherein X' is cycloalkyl of 3 to 6 carbon atoms, R and Z have the definition of claim 1, Alk and $Alk_1$ are individually alkyl of 1 to 3 carbon atoms and W is chlorine or fluorine.
6. A compound of claim 1 wherein Y is nitrogen.
* * * * *